US012740808B2

(12) United States Patent
Chen et al.

(10) Patent No.: US 12,740,808 B2
(45) Date of Patent: Sep. 22, 2026

(54) CONSUMABLE COMPONENT OF INJECTING PHYSIOLOGICAL MONITOR AND INJECTING PHYSIOLOGICAL MONITOR

(71) Applicants: Wei-Ting Chen, Taipei City (TW); Tzu-Chien Lai, Taipei City (TW); I-Hsuan Tsai, Taipei City (TW); Chien Chiu, Taipei City (TW)

(72) Inventors: Wei-Ting Chen, Taipei City (TW); Tzu-Chien Lai, Taipei City (TW); I-Hsuan Tsai, Taipei City (TW); Chien Chiu, Taipei City (TW)

(73) Assignee: COMPAL ELECTRONICS, INC., Taipei City (TW)

( * ) Notice: Subject to any disclaimer, the term of this patent is extended or adjusted under 35 U.S.C. 154(b) by 816 days.

(21) Appl. No.: 18/079,886

(22) Filed: Dec. 13, 2022

(65) Prior Publication Data

US 2023/0248391 A1 Aug. 10, 2023

(30) Foreign Application Priority Data

Feb. 8, 2022 (TW) ................................. 111104621

(51) Int. Cl.
*A61B 17/34* (2006.01)

(52) U.S. Cl.
CPC ................................ *A61B 17/3468* (2013.01)

(58) Field of Classification Search
CPC ............ A61B 17/3468; A61B 5/14503; A61B 5/14532; A61B 5/6848; A61M 5/20; A61M 5/2033
See application file for complete search history.

(56) References Cited

U.S. PATENT DOCUMENTS

| | | | | |
|---|---|---|---|---|
| 5,871,494 | A | 2/1999 | Simons et al. | |
| 2016/0030078 | A1* | 2/2016 | Lee | A61M 5/158 606/182 |
| 2016/0058344 | A1* | 3/2016 | Peterson | A61B 5/686 600/347 |
| 2019/0282137 | A1* | 9/2019 | Stafford | A61B 5/14503 |

FOREIGN PATENT DOCUMENTS

| | | |
|---|---|---|
| CN | 104792994 | 6/2017 |
| TW | I592140 | 7/2017 |
| TW | M591619 | 3/2020 |

* cited by examiner

*Primary Examiner* — Eric J Messersmith
(74) *Attorney, Agent, or Firm* — JCIPRNET

(57) ABSTRACT

A consumable component of an injecting physiological monitor includes a housing, an injecting module, a physiological monitor, and a carrier. The injecting module is movably assembled on the housing. The physiological monitor is disposed in the housing and located on a movement path of the injecting module. A part of a structure of the physiological monitor is accommodated in a part of a structure of the injecting module. The carrier is disposed in the housing and located on a movement path of the injecting module and the physiological monitor. The carrier and the physiological monitor are separated from each other and located on opposite sides of the housing. The housing and the injecting module are adapted to be assembled to an injector. The injector is adapted to drive the physiological monitor to be assembled to the carrier through the injecting module.

10 Claims, 8 Drawing Sheets

CONSUMABLE COMPONENT OF INJECTING PHYSIOLOGICAL MONITOR AND INJECTING PHYSIOLOGICAL MONITOR

CROSS-REFERENCE TO RELATED APPLICATION

This application claims the priority benefit of Taiwan application serial no. 111104621, filed on Feb. 8, 2022. The entirety of the above-mentioned patent application is hereby incorporated by reference herein and made a part of this specification.

BACKGROUND

Technical Field

The disclosure relates to a consumable component and a monitor, and more particularly, to a consumable component of an injecting physiological monitor and an injecting physiological monitor.

Description of Related Art

The monitor and the injecting body of the conventional injecting monitor are single-use consumables, which must be completely discarded after one use, resulting in excessive waste. In addition, the conventional injecting monitor usually has a hard needle used to puncture a surface of a living body and a protection element used to cover the hard needle. During transportation, use, and recycling, if the protection element is poorly manufactured or not fastened to cover the hard needle, leaving the hard needle exposed, there is a risk of injury to others. Therefore, how to reduce the amount of waste after each use of the injecting monitor and avoid a personal injury caused by the exposure of the hard needle is an urgent issue to be solved in the art.

SUMMARY

The disclosure provides a consumable component of an injecting physiological monitor and an injecting physiological monitor, which may reduce waste generated after each use of the injecting physiological monitor, and prevent a tip of an injecting module from being exposed and causing a personal injury.

A consumable component of an injecting physiological monitor in the disclosure includes a housing, an injecting module, a physiological monitor, and a carrier. The injecting module is removably assembled on the housing. The physiological monitor is disposed in the housing and located on a movement path of the injecting module. A part of a structure of the physiological monitor is accommodated in a part of a structure of the injecting module. The carrier is disposed in the housing and located on a movement path of the injecting module and the physiological monitor, and the carrier and the physiological monitor are separated from each other and located on opposite sides of the housing. The housing and the injecting module are adapted to be assembled to an injector. The injector is adapted to drive the physiological monitor to be assembled to the carrier through the injecting module.

In an embodiment of the disclosure, after the injector releases the physiological monitor and the carrier that are assembled from the housing to be injected to a surface of a living body, the injector resets the injecting module.

In an embodiment of the disclosure, the injecting module completes an assembly and injection of the physiological monitor and the carrier in a one-way and single stroke.

In an embodiment of the disclosure, the injecting module includes a puncture needle and a combination structure combined with each other. The puncture needle is located in the housing, and the combination structure protrudes out of the housing and is adapted to being assembled to the injector.

In an embodiment of the disclosure, the physiological monitor includes a sensing needle and an electronic component. The puncture needle has a guide groove. A first portion of the sensing needle is slidably accommodated in the guide groove, and a second portion of the sensing needle extends out of the guide groove from the first portion to be structurally combined and electrically connected to the electronic component.

In an embodiment of the disclosure, the carrier includes a through hole. When the physiological monitor is assembled to the carrier, the sensing needle and the puncture needle pass through the through hole and partially protrude from the housing.

In an embodiment of the disclosure, when the injector resets the injecting module, the injector drives the puncture needle to move into the housing and drives the combination structure to protrude out of the housing.

In an embodiment of the disclosure, the housing has a channel. The injecting module moves bidirectionally in the channel, and an outline of an outer shape of the physiological monitor is matched with an outline of an inner wall of the channel.

An injecting physiological monitor in the disclosure includes an injector and a consumable component. The consumable component includes a housing, an injecting module, a physiological monitor, and a carrier. The injecting module is movably assembled on the housing. The physiological monitor is disposed in the housing and located on a movement path of the injecting module. A part of a structure of the physiological monitor is accommodated in a part of a structure of the injecting module. The carrier is disposed in the housing and located on a movement path of the injecting module and the physiological monitor, and the carrier and the physiological monitor are separated from each other and located on opposite sides of the housing. The housing and the injecting module are configured to perform a usage mode after being assembled to the injector or to be dismounted from the injector. In the usage mode, the injector drives the injecting module to move relative to the housing to drive the physiological monitor to be assembled to the carrier.

In an embodiment of the disclosure, the injector includes a body, a driving member, a button, a first spring, and a handle. The housing is configured to be assembled to the body or dismounted from the body. The driving member is movably disposed in the body. The driving member has a first elastic arm to be engaged with the body or released from the body. The driving member has an engaging member, so that the injecting module is assembled to the engaging member or dismounted from the engaging member. The button is movably disposed on the body, and the first elastic arm is located on a movement path of the button. The handle is movably disposed on the body, and the handle is connected to the driving member. The first spring is connected to the driving member and the body, and the first spring is accommodated in the body.

In an embodiment of the disclosure, in a first state of the injector, the driving member is located at a first position, and the first elastic arm is engaged with the body. In a second state of the injector, the driving member is located at a second position, and the button presses the first elastic arm to release the driving member from the body. When the usage mode is performed, the button is subjected to an external force to convert the injector from the first state to the second state, and after the physiological monitor and the carrier that are assembled are released from the housing and injected to a surface of a living body, the external force is removed from the button to reset the injector to the first state.

In an embodiment of the disclosure, after the physiological monitor and the carrier that are assembled are released from the housing and injected to the surface of the living body, the injector resets the injecting module.

In an embodiment of the disclosure, the injecting module completes an assembly and injection of the physiological monitor and the carrier in a one-way and single stroke.

In an embodiment of the disclosure, the injecting module includes a puncture needle and a combination structure combined with each other. The puncture needle is located in the housing, and the combination structure protrudes out of the housing and is adapted to being assembled to the injector.

In an embodiment of the disclosure, the physiological monitor includes a sensing needle and an electronic component. The puncture needle has a guide groove. A first portion of the sensing needle is slidably accommodated in the guide groove, and a second portion of the sensing needle extends out of the guide groove from the first portion to be structurally combined and electrically connected to the electronic component.

In an embodiment of the disclosure, the carrier includes a through hole. When the physiological monitor is assembled to the carrier, the sensing needle and the puncture needle pass through the through hole and partially protrude from the carrier.

In an embodiment of the disclosure, when the injector resets the injecting module, the injector drives the puncture needle to move into the housing and drives the combination structure to protrude out of the housing.

In an embodiment of the disclosure, the housing has a channel. The injecting module moves bidirectionally in the channel, and an outline of an outer shape of the physiological monitor is matched with an outline of an inner wall of the channel.

Based on the above, the injecting physiological monitor in the disclosure is formed by the housing, the injecting module, and the physiological monitor that are in contact with the living body as the consumable component. The physiological monitor and the carrier are disposed separately, so that after the consumable component is assembled to the injector, in the process that the injector applies force to drive the injecting module, the assembly of the physiological monitor and the carrier and the injection to the surface of the living body are continuously completed. Accordingly, only the consumable component is required to be discarded after each injection, and the injector may be retained and reused to achieve the objective of reducing medical waste.

DETAILED DESCRIPTION OF DISCLOSED EMBODIMENTS

Figure 1A:
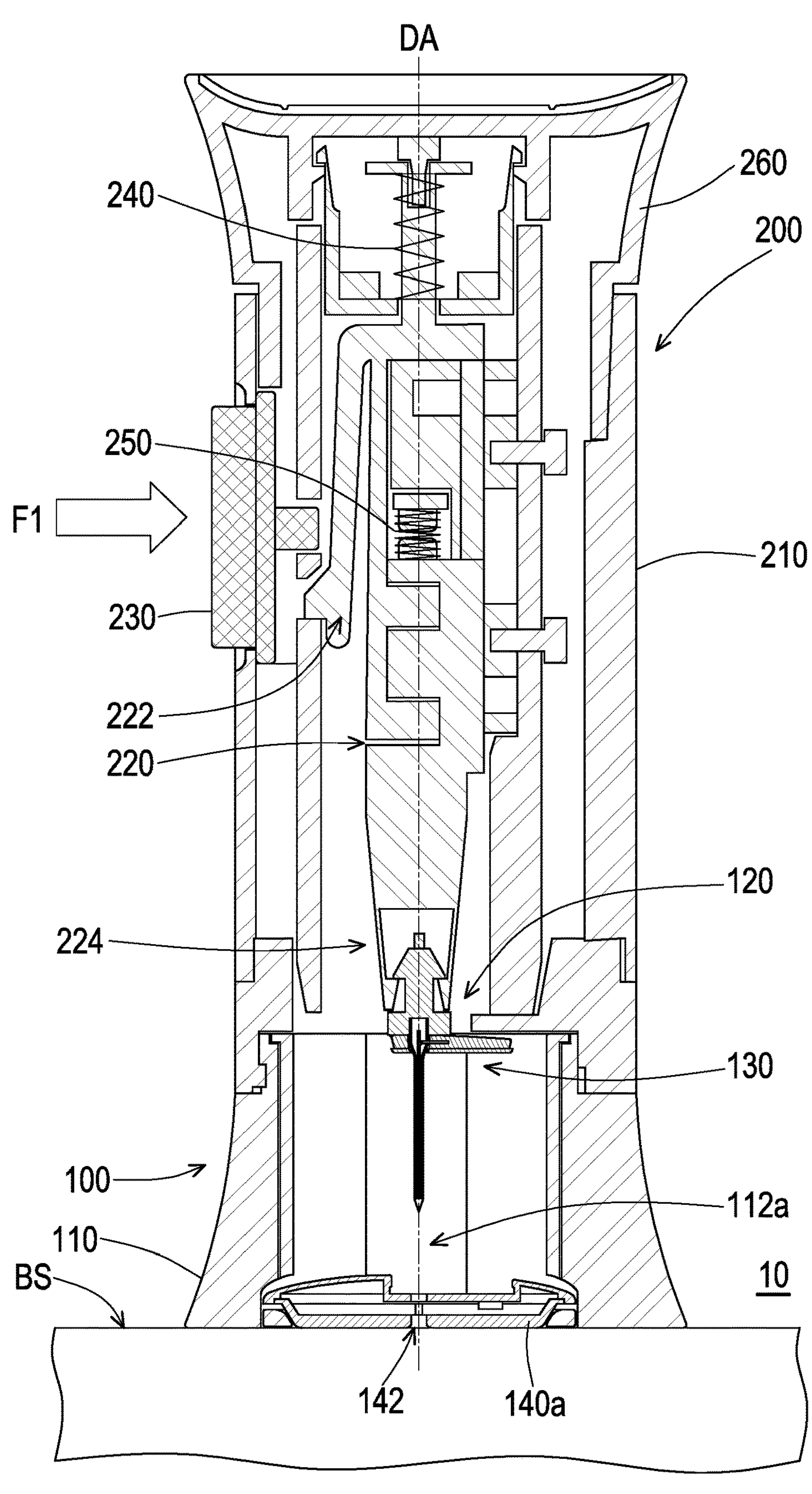
FIG. 1A is a schematic view of an injecting physiological monitor according to an embodiment of the disclosure.
Figure 1B:
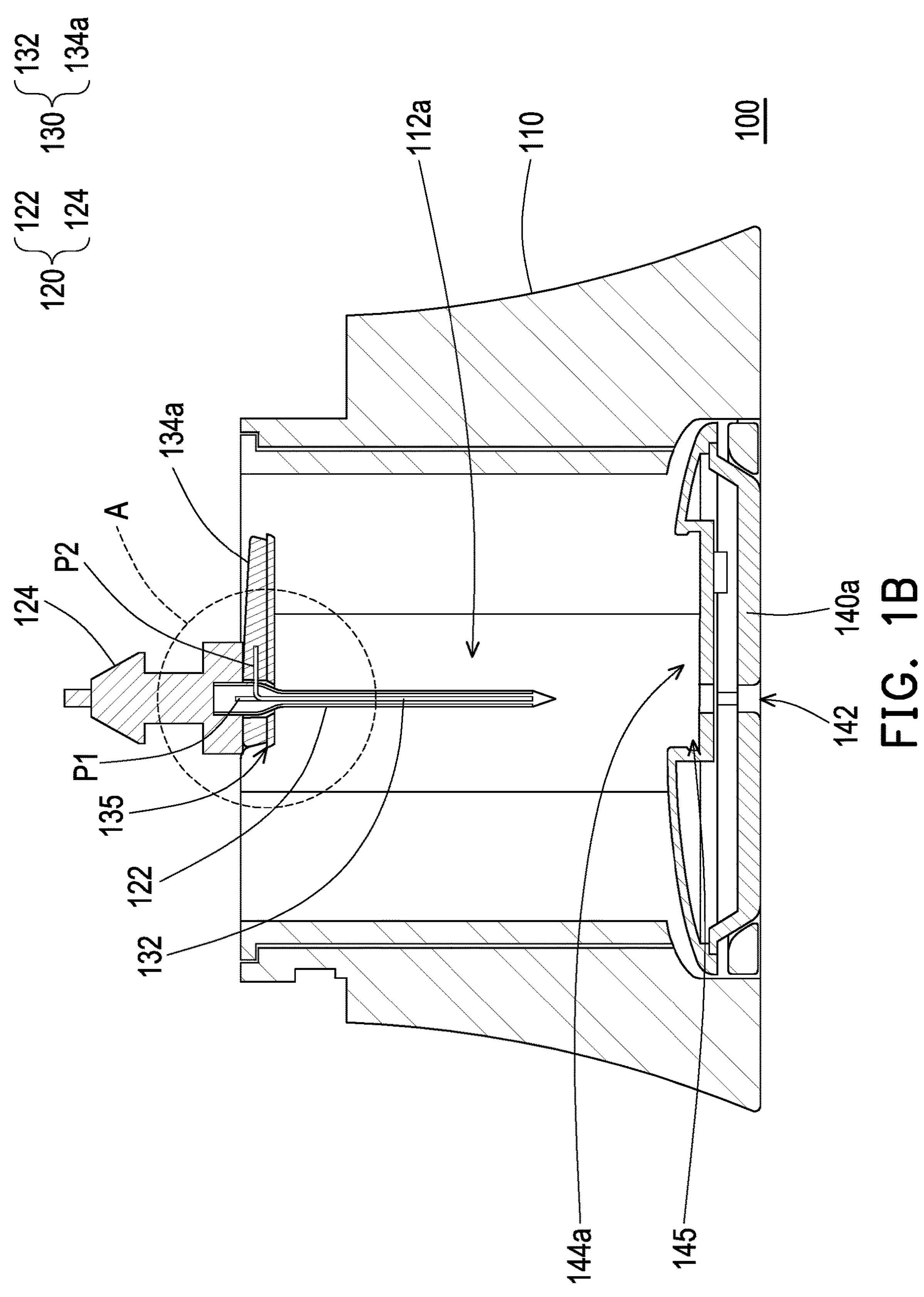
FIG. 1B is a schematic view of a consumable component in FIG. 1A.

FIG. 1A is a schematic view of an injecting physiological monitor according to an embodiment of the disclosure. FIG. 1B is a schematic view of a consumable component in FIG. 1A. Referring to both FIGS. 1A and 1B, an injecting physiological monitor 10 in this embodiment includes an injector 200 and a consumable component 100. The injector 200 includes a body 210 and a driving member 220. The consumable component 100 includes a housing 110 and an injecting module 120. The driving member 220 is movably disposed in the body 210, and the injecting module 120 is movably assembled on the housing 110. The housing 110 and the injecting module 120 are configured to be assembled to the injector 200 to perform a usage mode or to be dismounted from the injector 200. More specifically, the housing 110 is assembled to the body 210, and the injecting module 120 is assembled to the driving member 220. The driving member 220 is adapted to move bidirectionally between a first position (FIG. 1A) and a second position (FIG. 2) along a moving axis DA, so as to drive the injecting module 120 to move bidirectionally along the moving axis DA.

As shown in FIG. 1B, the consumable component 100 in this embodiment further includes a physiological monitor 130 and a carrier **140*a*. The physiological monitor 130 is movably disposed in the housing 110 and located on a movement path of the injecting module 120. A part of a structure of the physiological monitor 130 in this embodiment is accommodated in a part of a structure of the injecting module 120. The carrier 140*a* is disposed in the housing 110 and located on a movement path of the injecting module 120 and the physiological monitor 130. Before the usage mode is performed, the carrier 140*a* and the physiological monitor 130 are separated from each other and located on opposite sides of the housing 110. When the injector 200 is activated, the injecting module 120 is adapted to be pushed by the driving member 220 of the injector 200 to further push the physiological monitor 130 to move toward the carrier 140*a*, so as to assemble the physiological monitor 130 in an accommodating groove 144*a* of the carrier 140*a***.

Figure 1C:
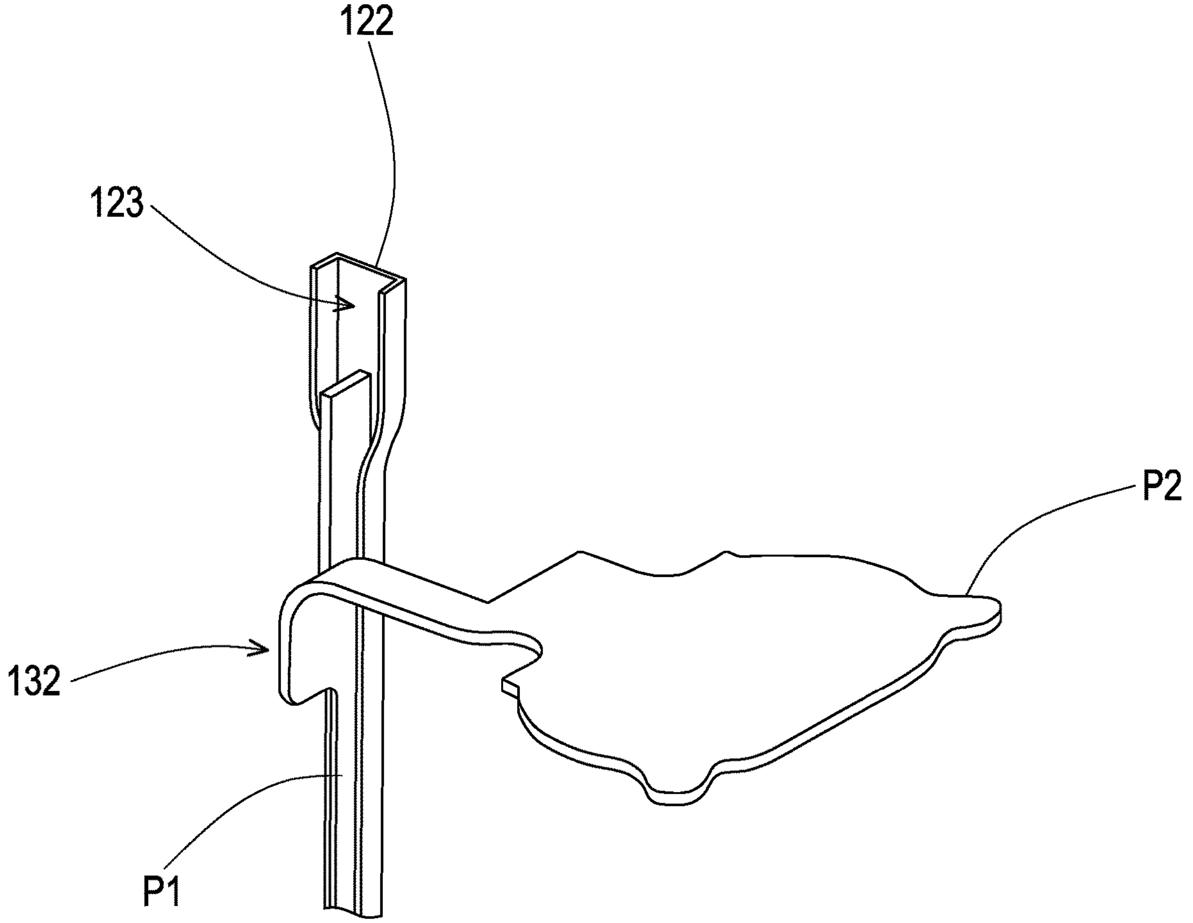
FIG. 1C illustrates some components of the consumable component in FIG. 1B from a perspective view.

FIG. 1C illustrates some components of the consumable component in FIG. 1B from a perspective view. Here, FIG. 1C shows structures of a puncture needle 122 and a sensing needle 132 in a region A in FIG. 1B from a perspective view. In order to clearly show a configuration relationship between the puncture needle 122 and the sensing needle 132, some components are omitted in FIG. 1C. Referring to FIGS. 1A to 1C together, the injecting module 120 in this embodiment includes the puncture needle 122 and a combination structure 124 combined with each other, and the physiological monitor 130 includes the sensing needle 132 and an electronic component **134*a*. As shown in FIG. 1A, when the consumable component 100 is assembled to the injector 200, and the injector 200 is in a first state, the puncture needle 122 is located in the housing 110, and the combination structure 124 protrudes out of the housing 110 and is assembled to the driving member 220 of the injector 200**.

As shown in FIG. 1C, the sensing needle 132 is, for example, formed by stamping and bending a metal plate, but the disclosure is not limited thereto. The sensing needle 132 has a first portion P1 and a second portion P2 bent relative to the first portion P1, and the first portion P1 and the second portion P2 are not parallel to each other. The puncture needle 122 has a guide groove 123. The first portion P1 of the sensing needle 132 is slidably accommodated in the guide groove 123, so that the puncture needle 122 may be separated from the sensing needle 132. The second portion P2 extends from the first portion P1 away from the guide groove 123, and a structure of the second portion P2 is combined and electrically connected to the electronic component 134*a*. Here, an area of the second portion P2 is significantly greater than that of the first portion P1, so as to improve a structural bonding strength of the second portion P2 and the electronic component 134*a* and be conducive to maintaining a stable electrical connection between the second portion P2 and the electronic component 134*a*.

Referring back to FIG. 1A, the injector 200 further includes a button 230, a second spring 240, a first spring 250, and a handle 260, and the driving member 220 has a first elastic arm 222 and an engaging member 224. Here, the engaging member 224 may be regarded as a second elastic arm of the driving member 220. The button 230 and the handle 260 are movably disposed on the body 210. The first elastic arm 222 is located on a movement path of the button 230, and the handle 260 may move bidirectionally relative to the body 210 along the moving axis DA. The combination structure 124 of the injecting module 120 is engaged with the engaging member 224. In this embodiment, the movement path of the button 230 is perpendicular to the moving axis DA. The second spring 240 and the first spring 250 are respectively connected to the driving member 220 and the body 210, and the second spring 240 and the first spring 250 are located at different positions on the same moving axis DA of the driving member 220. More specifically, the second spring 240 abuts between the handle 260 and the driving member 220. The first spring 250 is connected to the driving member 220 and the body 210. The first spring 250 is accommodated in the body 210, and a driving direction of an elastic force of the second spring 240 is opposite to a driving direction of an elastic force of the first spring 250. In this embodiment, the elastic force of the first spring 250 is configured to move the driving member 220 downward (i.e., toward a surface BS of a living body).

As shown in FIG. 1A, before the button 230 receives force, the injector 200 is in the first state, and the driving member 220 is in the first position. In the first state, the button 230 protrudes from the body 210. The first elastic arm 222 is engaged with the body 210, and the combination structure 124 and the engaging member 224 are located in the body 210. At this time, the elastic force of the first spring 250 is greater than that of the second spring 240, but the driving member 220 is maintained at the first position because the first elastic arm 222 is engaged with the body 210. Here, the injecting physiological monitor 10 is placed on the surface BS of the living body and ready to perform injection.

Figure 2:
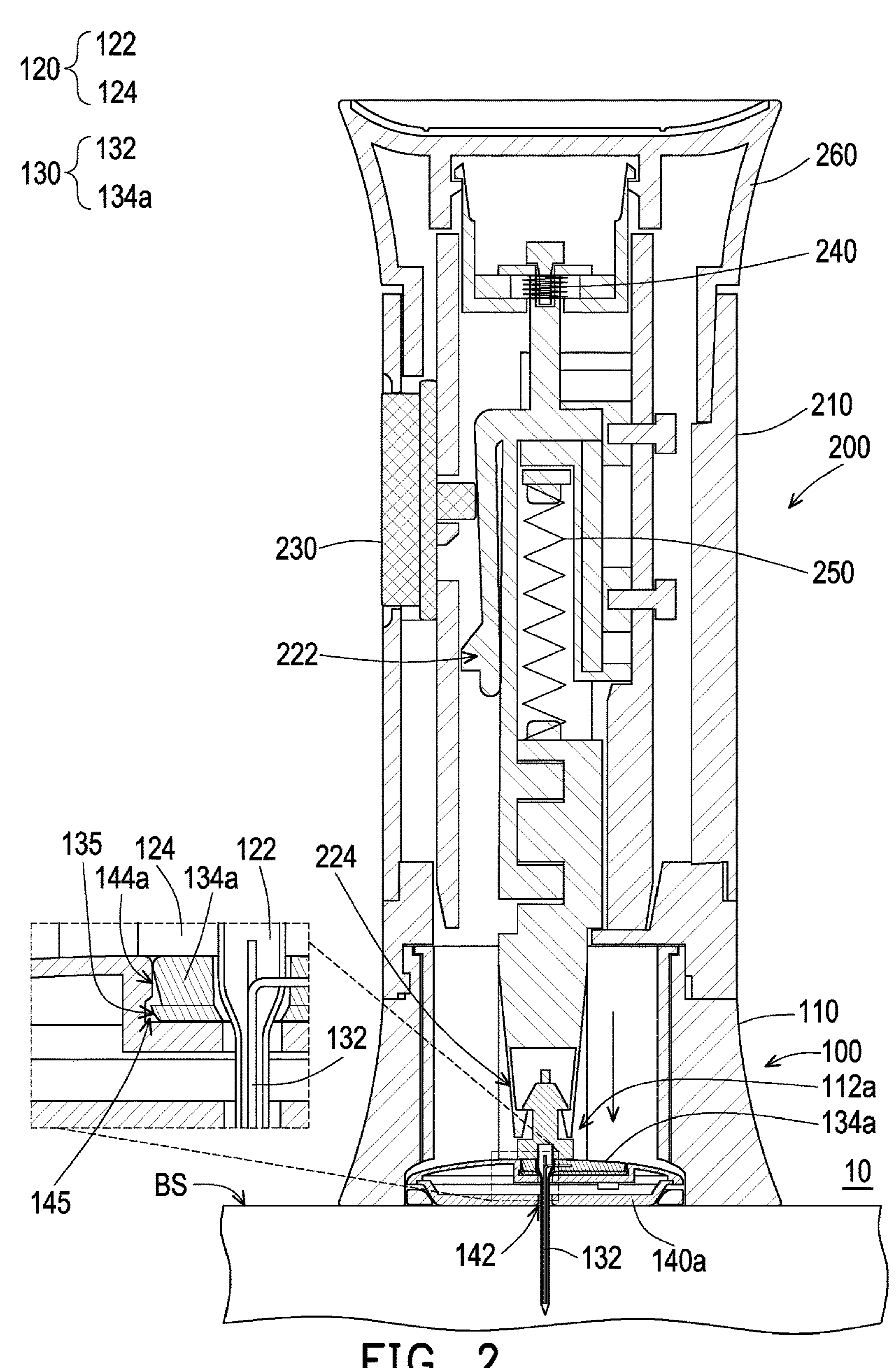
FIG. 2 is a schematic view of the injecting physiological monitor in FIG. 1A during injection.

FIG. 2 is a schematic view of the injecting physiological monitor in FIG. 1A during injection. Referring to both FIG. 1A and FIG. 2, a user applies an external force F1 to the button 230 (FIG. 1A), so that the injector 200 is converted from the first state shown in FIG. 1A to a second state shown in FIG. 2 to perform the usage mode. As shown in FIG. 2, the button 230 is pushed into the body 210 by the external force F1 and presses the first elastic arm 222 to release an engaging relationship with the body 210. At this time, the driving member 220 is driven to the second position due to the elastic force of the first spring 250. Then, the driving member 220 pushes the injecting module 120 and the physiological monitor 130 to move toward the carrier 140*a* until the physiological monitor 130 is assembled to the carrier 140*a*, and then the injecting module 120 is used to inject the physiological monitor 130 and the carrier 140*a* that are assembled onto the surface BS of the living body, so as to perform an assembly and injection of the physiological monitor 130 and the carrier 140*a*. During this process, the elastic force accumulated by the first spring 250 in FIG. 1A is configured to perform the assembly and injection, and further drives the second spring 240 to deform until the second spring 240 and the first spring 250 are in a state of force equilibrium.

Specifically, during a process of the assembly and injection of the physiological monitor 130 and the carrier 140*a*, the engaging member 224 of the driving member 220 and the combination structure 124 of the injecting module 120 extend into a channel 112*a* of the housing 110, and the puncture needle 122 of the injecting module 120 and the sensing needle 132 of the physiological monitor 130 pass through a through hole 142 of the carrier 140*a*, partially protrude from the carrier 140*a*, and puncture the surface BS of the living body. In this embodiment, the channel 112*a* is adapted to serve as a guide path to travel in housing 110 for the engaging member 224 of the driving member 220 and the combination structure 124, but the disclosure is not limited thereto.

In brief, the driving member 220 and the injecting module 120 in this embodiment complete the assembly and injection of the physiological monitor 130 and the carrier 140*a* in a one-way and single stroke in the channel 112*a*. A movement of the driving member 220 from the first position to the second position is a one-way stroke, and during the process of the assembly and injection of the physiological monitor 130 and the carrier 140*a*, only the button 230 is required to be pressed without additional operations, which is the single stroke.

A needle body (e.g., the puncture needle 122 and/or the sensing needle 132) of the conventional injecting physiological monitor is exposed to an external environment, and an additional protection element is required to cover the needle body to prevent the needle body from stabbing the user or a processing personnel. Therefore, in the conventional injecting physiological monitor, the protection element covering the needle body has to be removed before the injection, which is a multi-stage stroke. In this embodiment, since the needle bodies (the puncturing needle 122 and the sensing needle 132) are all accommodated in the housing 110 before the assembly and injection, no additional protection element is required. Therefore, in the injecting physiological monitor 10 in this embodiment, only the button 230 is required to be pressed to complete the injection, while the needle body is prevented from being exposed.

Referring back to FIG. 2, in this embodiment, a shape of the accommodating groove 144*a* of the carrier 140*a* is matched with a shape of the electronic component 134*a*. As shown in an enlarged view in FIG. 2, the electronic component 134*a* has a convex portion 135, and the accommodating groove 144*a* is provided with a concave groove 145. When the electronic component 134*a* is assembled to the accommodating groove 144*a*, the convex portion 135 is engaged and matched with the concave groove 145, so that the electronic component 134*a* is stably accommodated in the carrier 140*a*. At this time, the injecting physiological monitor 10 has completed the injection of the physiological monitor 130 and the carrier 140*a*. The physiological monitor 130 and the carrier 140*a* are attached to the surface BS of the living body to obtain physiological information of the living body. For example, the physiological monitor 130 and the carrier 140*a* in this embodiment may be used for continuous blood glucose detection. A method of attaching the carrier 140*a* to the surface BS of the living body is, for example, through a double-sided medical tape, but the disclosure is not limited thereto.

Figure 3:
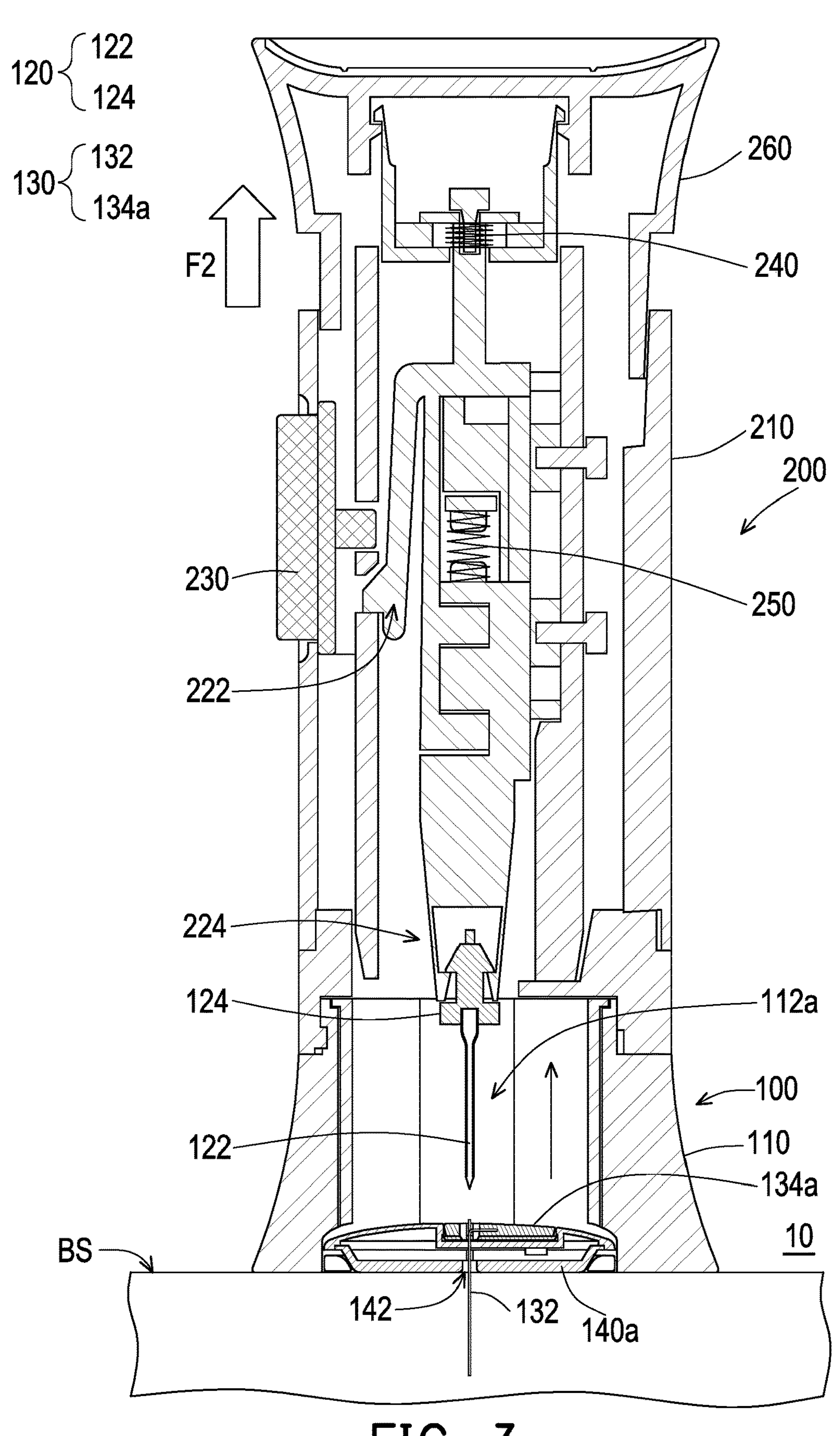
FIG. 3 is a schematic view of the injecting physiological monitor in FIG. 2 during resetting.
Figure 4:
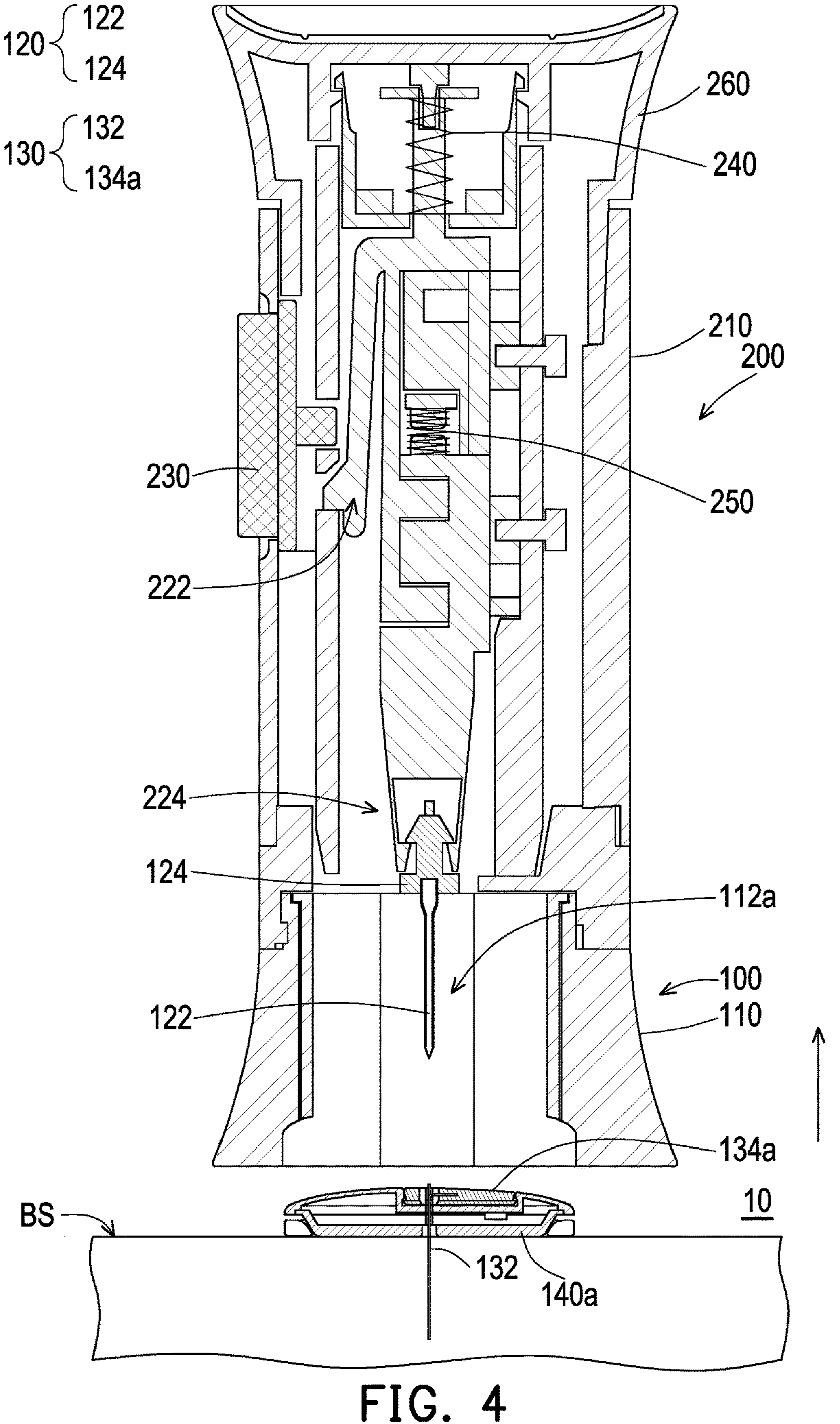
FIG. 4 is a schematic view of the injecting physiological monitor in FIG. 3 separated from some components.

FIG. 3 is a schematic view of the injecting physiological monitor in FIG. 2 during resetting. FIG. 4 is a schematic view of the injecting physiological monitor in FIG. 3 separated from some components. Referring to FIGS. 2 to 4 together, FIG. 3 shows a process of resetting the driving member 220 from the second position in FIG. 2 to the first position. In FIG. 4, the driver 220 is reset, and the injecting physiological monitor 10 is separated from the physiological monitor 130 and the carrier 140*a*. After the injection of the physiological monitor 130 and the carrier 140*a* (FIG. 2) is completed, as shown in FIG. 3, the external force F1 is removed from the button 230, and an external force F2 is applied to stretch the handle 260 upward, so that the second spring 240 is compressed and pulls the driving member 220 and the injecting module 120 to be reset upward. The first elastic arm 222 moves upward along with the driving member 220 to be reset and engaged with the body 210. At this time, the handle 260 is in a state of sliding upward relative to the body 210. Specifically, the engaging member 224 drives the injecting module 120 to move in a direction of an arrow in the channel 112*a*. Here, the injecting module 120 is separated from the physiological monitor 130 and the carrier 140*a*.

Next, the external force F2 is removed to reset the handle 260. As shown in FIG. 4, after the external force F2 is removed, the second spring 240 compressed by the external force F2 releases prestress, so that the handle 260 slides downward relative to the body 210 and returns to an initial state. In light of the above, with the rebound force of the second spring 240, the overstretched handle 260 may be rebounded and reset to an initial position. At this time, there is no large gap between the handle 260 and the body 210, and a risk of pinching hands of the user when pressing the button 230 may be avoided.

After the handle 260, the driving member 220, and the injecting module 120 are reset back to the positions shown in FIG. 4, the injecting physiological monitor 10 is reset. It is worth mentioning that when the driving member 220 is reset, the first elastic arm 222 moves upward and pushes the button 230, so that the button 230 returns from the position shown in FIG. 2 to the position shown in FIG. 3 and protrudes out of the body 210. The user may determine whether the driving member 220 and the injecting module 120 are reset according to a position of the button 230. After the injector 200 and the injecting module 120 are reset, the injector 200 is lifted to separate the physiological monitor 130 and the carrier 140*a* that are assembled from the housing 110. At this time, the puncture needle 122 is accommodated in the housing 110 without being exposed, so as to avoid stabbing others. In other words, the puncture needle 122 is always hidden in the channel 112*a* of the housing 110 during non-injection.

Figure 5:
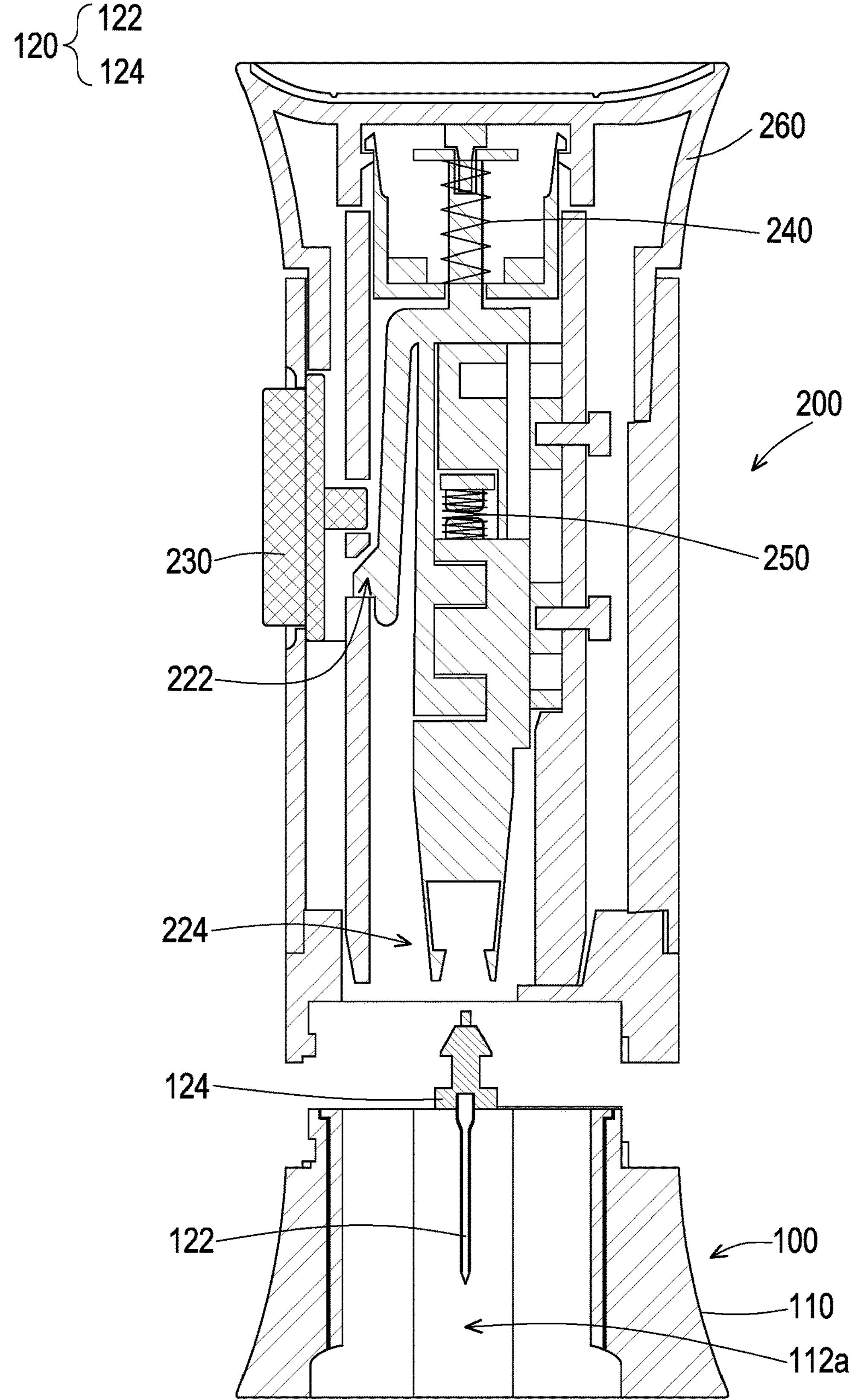
FIG. 5 is a schematic view of an injector in FIG. 4 separated from a consumable component.

FIG. 5 is a schematic view of an injector in FIG. 4 separated from a consumable component. Referring to FIG. 5, after the puncture needle 122 of the consumable component 100 is reset back into the housing 110, the user may remove the housing 110 of the consumable component 100 together with the injecting module 120 from the injector 200. The consumable component 100 in this embodiment is a single-use disposable component, while the injector 200 is reusable. In other words, in the injecting physiological monitor 10, only the consumable component 100 is required to be discarded after each use, and the injector 200 may be connected to the new consumable component 100 to perform the injection again, so as to reduce the amount of waste after each use. In addition, it may be seen from a driving method of the injecting physiological monitor 10 that the puncture needle 122 protrudes out of the housing 110 and punctures the surface BS of the living body only when the driving member 220 is at the second position (FIG. 2), and when the consumable component 100 is disposed on the injector 200 (FIG. 1A), or the consumable component 100 is dismounted from the injector 200 (FIG. 5), the puncture needle 122 is always accommodated in the housing 110. With this design, the puncture needle 122 may be prevented from being exposed to stab others, and it is not necessary to use the additional protection element to cover the puncture needle 122. Therefore, in the injecting physiological monitor 10 in this embodiment, the assembly and injection of the physiological monitor 130 and the carrier 140*a* may be completed through the one-way and single stroke.

Figure 6A:
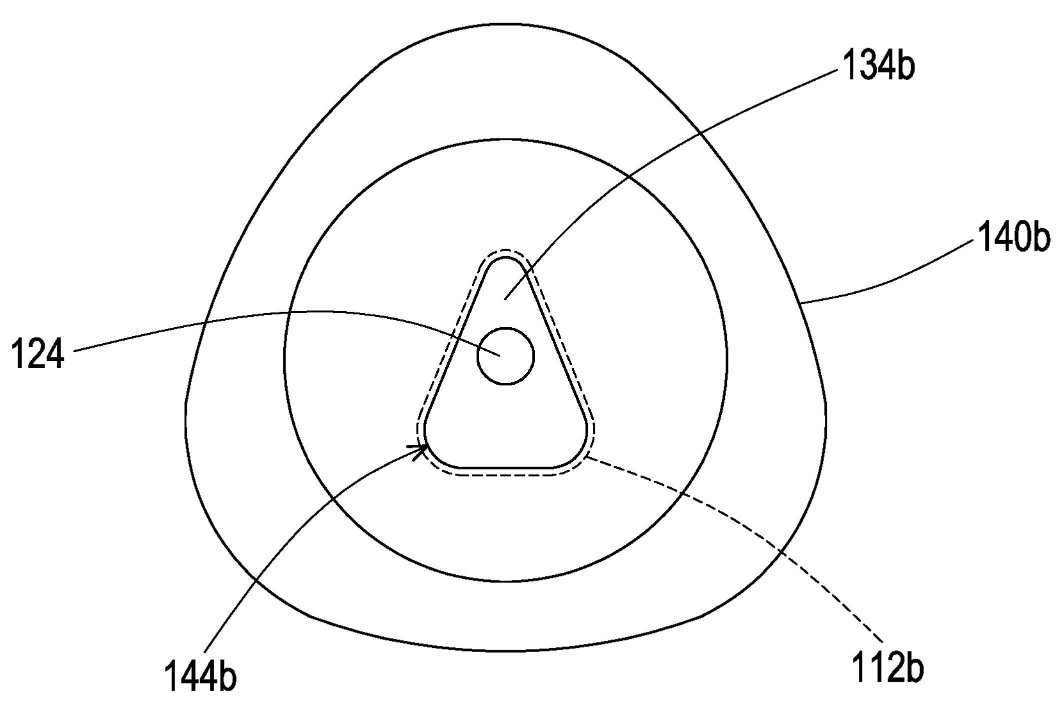
FIGS. 6A and 6B respectively illustrates consumable components in different embodiments.
Figure 6B:
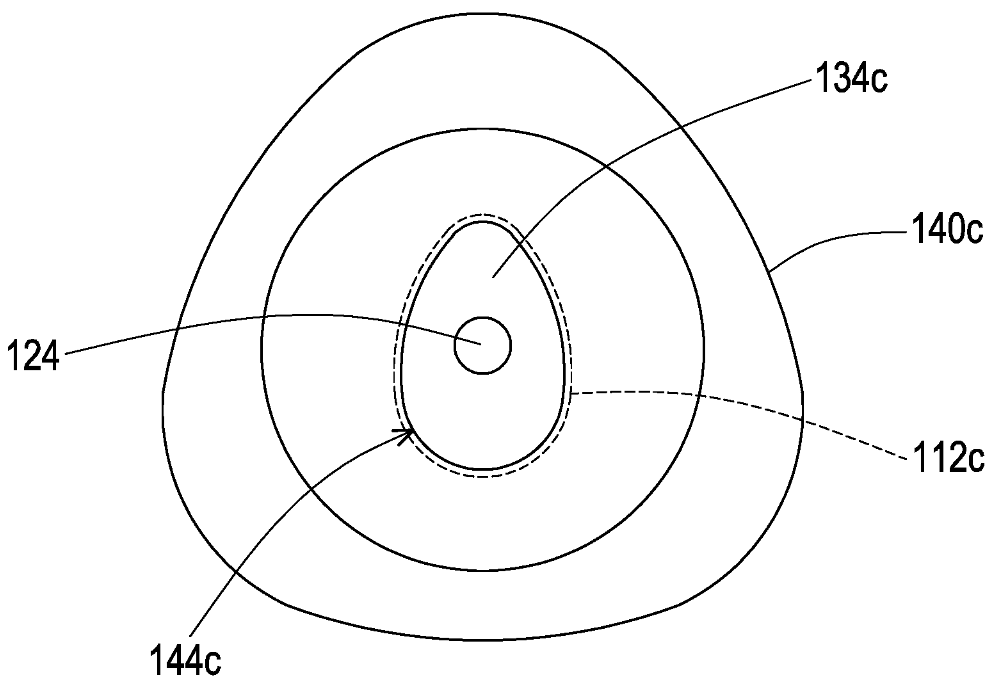

FIGS. 6A and 6B respectively illustrates consumable components in different embodiments. FIGS. 6A and 6B are top views providing electronic components 134*b* and 134*c*, the combination structure 124, and outlines of inner walls (shown in dashed lines) of channels 112*b* and 112*c* of the housing. Referring to both FIGS. 6A and 6B, the outlines of the inner walls of the channels 112*b* and 112*c* are respectively matched with outlines of outer shapes of the electronic components 134*b* and 134*c*, so as to provide a foolproof effect when the electronic components 134*b* and 134*c* are assembled into the housing 110. Specifically, the channels 112*b* and 112*c* are adapted to prevent rotation of the electronic components 134*b* and 134*c* when the electronic components 134*b* and 134*c* move in the channels 112*b* and 112*c*.

Here, the outline of the inner wall of the channel 112*b* is in a triangle shape, and the outline of the inner wall of the channel 112*c* is in a shape of an egg. However, the disclosure is not limited thereto. In light of the above, shapes of the channels 112*b* and 112*c* may be changed according to the outlines of the outer shapes of the electronic components 134*b* and 134*c*. In addition, the channel 112*a* in FIG. 1A is configured to guide the movement of the driving member 220 and the injecting module 120, and is not matched with the outline of the outer shape of the electronic component 134*a*. The user may dispose the appropriate channels 112*a*, 112*b*, and 112*c* according to their needs.

Based on the above, the injecting physiological monitor in the disclosure includes the injector and the consumable component that may be dismounted from the injector. The injecting module, the physiological monitor, and the carrier that are in contact with the surface of the living body are all disposed in the consumable component, and the carrier and the physiological monitor are separated from each other and located on the opposite sides of the housing. The injecting module may complete the assembly and injection of the physiological monitor and the carrier through the one-way and single stroke. Only the consumable component that is in contact with the surface of the living body is required to be discarded after each injection, and the injector is reusable, so as to reduce the waste generated after each use. In addition, by separating the injecting module from the physiological monitor and the carrier, the puncture needle of the injecting module only protrudes from the housing in the usage mode, and is reset back to the housing after the usage mode, so as to ensure that the puncture needle is not exposed and cause a personal injury.

What is claimed is:

1. An injecting physiological monitor, comprising:

an injector; and a consumable component, comprising:

a housing;

an injecting module movably assembled on the housing;

a physiological monitor disposed in the housing and located on a movement path of the injecting module, wherein a part of a structure of the physiological monitor is accommodated in a part of a structure of the injecting module; and a carrier disposed in the housing and located on a movement path of the injecting module and the physiological monitor, wherein the carrier and the physiological monitor are separated from each other and located on opposite sides of the housing, wherein the housing and the injecting module are configured to perform a usage mode after being assembled to the injector or to be dismounted from the injector, and in the usage mode, the injector drives the injecting module to move relative to the housing to drive the physiological monitor to be assembled to the carrier, the physiological monitor and the carrier are assembled together within the housing.

2. The injecting physiological monitor according to claim 1, wherein the injector comprises a body, a driving member, a button, a first spring, and a handle, the housing is configured to be assembled to the body or dismounted from the body, the driving member is movably disposed in the body, the driving member has a first elastic arm to be engaged with the body or released from the body, the driving member has an engaging member, so that the injecting module is assembled to the engaging member or dismounted from the engaging member, the button is movably disposed on the body, and the first elastic arm is located on a movement path of the button, the handle is movably disposed on the body, and the handle is connected to the driving member, the first spring is connected to the driving member and the body, and the first spring is accommodated in the body.

3. The injecting physiological monitor according to claim 2, wherein in a first state of the injector, the driving member is located at a first position, and the first elastic arm is engaged with the body, in a second state of the injector, the driving member is located at a second position, and the button presses the first elastic arm to release the driving member from the body, when the usage mode is performed, the button is subjected to an external force to convert the injector from the first state to the second state, and after the physiological monitor and the carrier that are assembled are released from the housing and injected to a surface of a living body, the external force is removed from the button to reset the injector to the first state.

4. The injecting physiological monitor according to claim 1, wherein after the physiological monitor and the carrier that are assembled are released from the housing and injected to a surface of a living body, the injector resets the injecting module.

5. The injecting physiological monitor according to claim 4, wherein the injecting module completes an assembly and injection of the physiological monitor and the carrier in a one-way and single stroke.

6. The injecting physiological monitor according to claim 4, wherein the injecting module comprises a puncture needle and a combination structure combined with each other, the puncture needle is located in the housing, and the combination structure protrudes out of the housing and is adapted to being assembled to the injector.

7. The injecting physiological monitor according to claim 6, wherein the physiological monitor comprises a sensing needle and an electronic component, the puncture needle has a guide groove, a first portion of the sensing needle is slidably accommodated in the guide groove, and a second portion of the sensing needle extends out of the guide groove from the first portion to be structurally combined and electrically connected to the electronic component.

8. The injecting physiological monitor according to claim 7, wherein the carrier comprises a through hole, and when the physiological monitor is assembled to the carrier, the sensing needle and the puncture needle pass through the through hole and partially protrude from the housing.

9. The injecting physiological monitor according to claim 6, wherein when the injector resets the injecting module, the injector drives the puncture needle to move into the housing and drives the combination structure to protrude out of the housing.

10. The injecting physiological monitor according to claim 1, wherein the housing has a channel, the injecting module moves bidirectionally in the channel, and an outline of an outer shape of the physiological monitor is matched with an outline of an inner wall of the channel.

* * * * *